(12) United States Patent
Moore

(10) Patent No.: US 11,096,802 B2
(45) Date of Patent: Aug. 24, 2021

(54) INTERVERTEBRAL TRIAL WITH MARKER

(71) Applicant: K2M, Inc., Leesburg, VA (US)

(72) Inventor: Jennifer Moore, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 206 days.

(21) Appl. No.: 16/290,100

(22) Filed: Mar. 1, 2019

(65) Prior Publication Data
US 2019/0269527 A1    Sep. 5, 2019

Related U.S. Application Data

(60) Provisional application No. 62/638,099, filed on Mar. 3, 2018.

(51) Int. Cl.
*A61F 2/46* (2006.01)
*A61B 90/00* (2016.01)

(52) U.S. Cl.
CPC ............ *A61F 2/4684* (2013.01); *A61B 90/39* (2016.02); *A61F 2/4657* (2013.01); *A61B 2090/3966* (2016.02); *A61F 2/4611* (2013.01); *A61F 2002/4658* (2013.01)

(58) Field of Classification Search
CPC ....... A61F 2/4684; A61F 2/4657; A61B 90/06
See application file for complete search history.

(56) References Cited

U.S. PATENT DOCUMENTS

| | | | |
|---|---|---|---|
| 5,989,291 A | 11/1999 | Ralph et al. | |
| 6,428,544 B1 | 8/2002 | Ralph et al. | |
| 6,436,102 B1 | 8/2002 | Ralph et al. | |
| 6,440,142 B1 | 8/2002 | Ralph et al. | |
| 6,447,548 B1 | 9/2002 | Ralph et al. | |
| 6,468,310 B1 | 10/2002 | Ralph et al. | |
| 6,471,725 B1 | 10/2002 | Ralph et al. | |
| 6,478,801 B1 | 11/2002 | Ralph et al. | |
| 6,527,806 B2 | 3/2003 | Ralph et al. | |
| 6,554,864 B2 | 4/2003 | Ralph et al. | |
| 6,562,047 B2 | 5/2003 | Ralph et al. | |
| 6,706,068 B2 | 3/2004 | Ferree | |
| 6,740,117 B2 | 5/2004 | Ralph et al. | |
| 6,863,688 B2 | 3/2005 | Ralph et al. | |
| 6,863,689 B2 | 3/2005 | Ralph et al. | |
| 6,865,954 B2 | 3/2005 | Zubok et al. | |
| 6,887,273 B2 | 5/2005 | Ralph et al. | |

(Continued)

OTHER PUBLICATIONS

Inventor Gordon D. Donald, Fairhaven, NJ, Application No. 60499747 filed Sep. 3, 2003, Artificial cervical disc having a central bearing suface and radially disposed elastomer.

*Primary Examiner* — Andrew Yang
(74) *Attorney, Agent, or Firm* — Lerner, David, Littenberg, Krumholz & Mentlik, LLP

(57) ABSTRACT

In one embodiment, an intervertebral trial includes a front surface, a top surface, a bottom surface, a first side surface and a second side surface that collectively define an internal space. The internal space includes at least one marker structure attached to at least one of the top surface, the bottom surface, the first side surface and the second side surface. The at least one marker structure indicates a dimension of the intervertebral trial. Additionally, the at least one marker structure is spatially representative of the dimension when measured relative to one of the front surface, the top surface, the bottom surface, the first side surface or the second side surface.

20 Claims, 7 Drawing Sheets

(56) References Cited

U.S. PATENT DOCUMENTS

| | | | |
|---|---|---|---|
| 6,887,274 B2 | 5/2005 | Ralph et al. |
| 6,896,676 B2 | 5/2005 | Zubok et al. |
| 6,908,484 B2 | 6/2005 | Zubok et al. |
| 6,918,934 B2 | 7/2005 | Ralph et al. |
| 6,932,844 B2 | 8/2005 | Ralph et al. |
| 6,989,032 B2 | 1/2006 | Errico et al. |
| 7,014,658 B2 | 3/2006 | Ralph et al. |
| 7,022,139 B2 | 4/2006 | Errico et al. |
| 7,048,763 B2 | 5/2006 | Ralph et al. |
| 7,115,132 B2 | 10/2006 | Errico et al. |
| 7,122,055 B2 | 10/2006 | Ralph et al. |
| 7,169,182 B2 | 1/2007 | Errico et al. |
| 7,208,014 B2 | 4/2007 | Ralph et al. |
| 7,214,244 B2 | 5/2007 | Zubok et al. |
| 7,217,292 B2 | 5/2007 | Ralph et al. |
| 7,223,291 B2 | 5/2007 | Errico et al. |
| 7,235,081 B2 | 6/2007 | Errico et al. |
| 7,452,380 B2 | 11/2008 | Zubok et al. |
| 7,491,241 B2 | 2/2009 | Errico et al. |
| 7,550,008 B2 | 6/2009 | Ralph et al. |
| 7,563,285 B2 | 7/2009 | Ralph et al. |
| 7,575,576 B2 | 8/2009 | Zubok et al. |
| 7,604,664 B2 | 10/2009 | Ralph et al. |
| 7,635,368 B2 | 12/2009 | Errico et al. |
| 7,662,182 B2 | 2/2010 | Zubok et al. |
| 7,695,478 B2 | 4/2010 | Ralph et al. |
| 7,722,675 B2 | 5/2010 | Ralph et al. |
| 7,811,287 B2 | 10/2010 | Errico et al. |
| 7,918,891 B1 | 4/2011 | Curran et al. |
| 7,951,202 B2 | 5/2011 | Ralph et al. |
| 8,038,713 B2 | 10/2011 | Ferree |
| 8,147,499 B2 | 4/2012 | Zubok et al. |
| 8,187,334 B2 | 5/2012 | Curran et al. |
| 8,231,628 B2 | 7/2012 | Zubok et al. |
| 8,246,686 B1 | 8/2012 | Curran et al. |
| 8,277,507 B2 | 10/2012 | Ferree et al. |
| 8,323,292 B2 | 12/2012 | Dudasik et al. |
| 8,343,162 B2 | 1/2013 | Ralph et al. |
| 8,361,156 B2 | 1/2013 | Curran et al. |
| 8,366,775 B2 | 2/2013 | Errico et al. |
| 8,425,609 B2 | 4/2013 | Zubok et al. |
| 8,470,041 B2 | 6/2013 | Ferree |
| 8,545,564 B2 | 10/2013 | Errico et al. |
| 8,574,301 B2 | 11/2013 | Curran et al. |
| 8,579,911 B2 | 11/2013 | Dudasik |
| 8,608,804 B2 | 12/2013 | Curran et al. |
| 8,685,105 B2 | 4/2014 | Curran et al. |
| 8,777,959 B2 | 7/2014 | Errico et al. |
| 8,814,940 B2 | 8/2014 | Curran et al. |
| 9,095,451 B2 | 8/2015 | Errico et al. |
| 9,180,021 B2 | 11/2015 | Curran et al. |
| 9,226,837 B2 | 1/2016 | Errico et al. |
| 9,474,627 B2 | 10/2016 | Curran et al. |
| 9,744,053 B2 | 8/2017 | Curran et al. |
| 2013/0110121 A1* | 5/2013 | Lemaitre ............... A61B 90/06 606/102 |
| 2015/0342757 A1* | 12/2015 | Lomeli ................ A61F 2/46 623/17.16 |
| 2018/0014946 A1 | 1/2018 | Curran et al. |

* cited by examiner

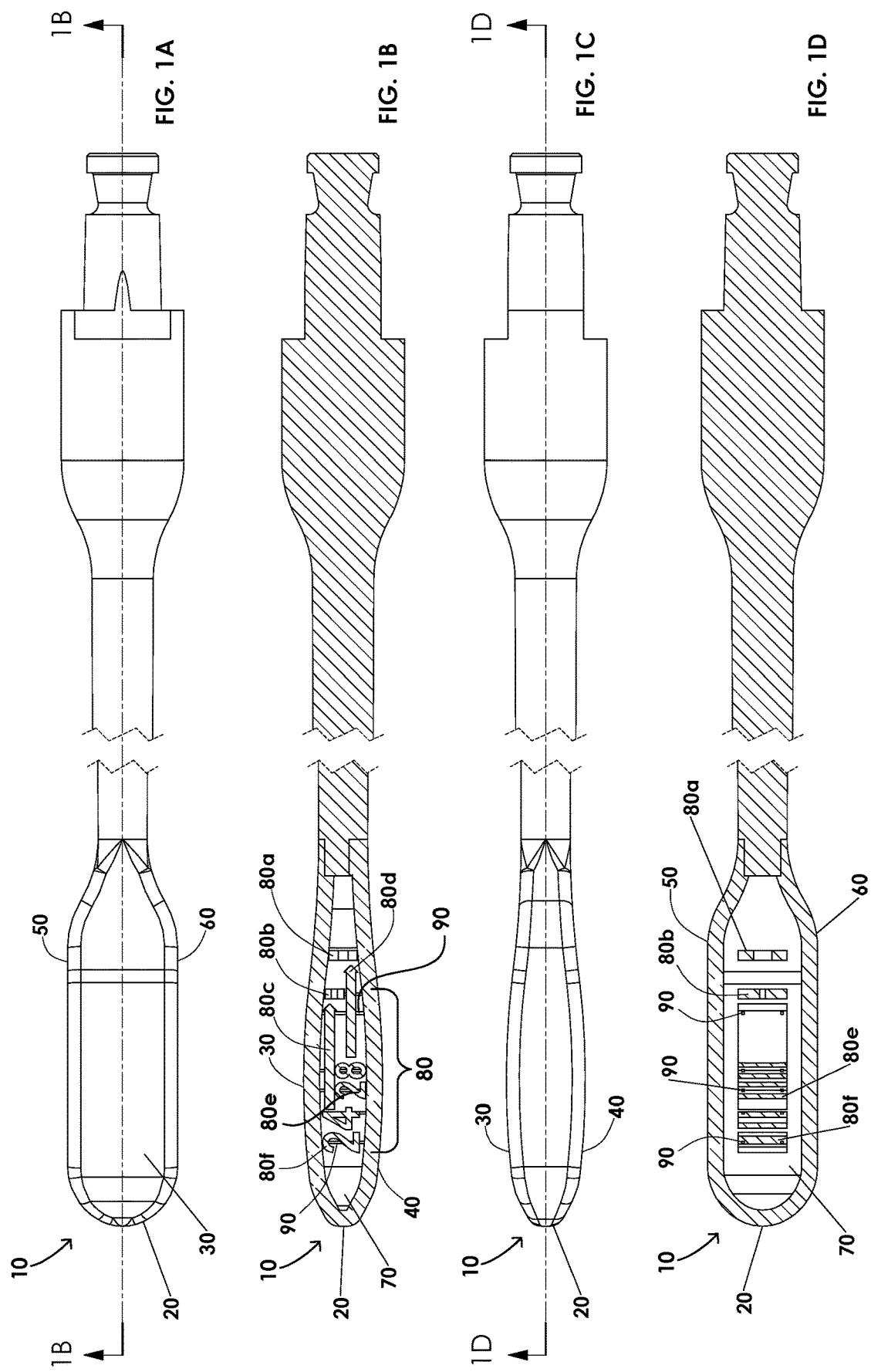

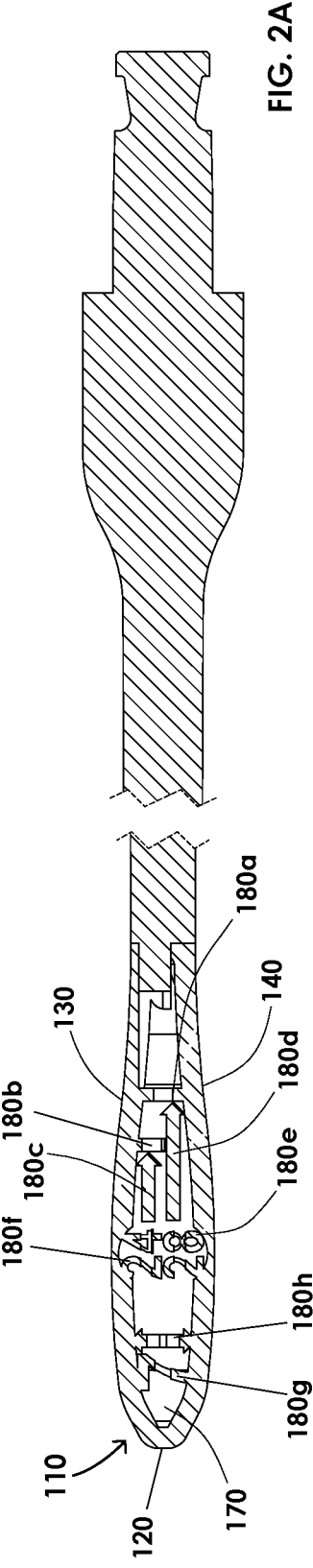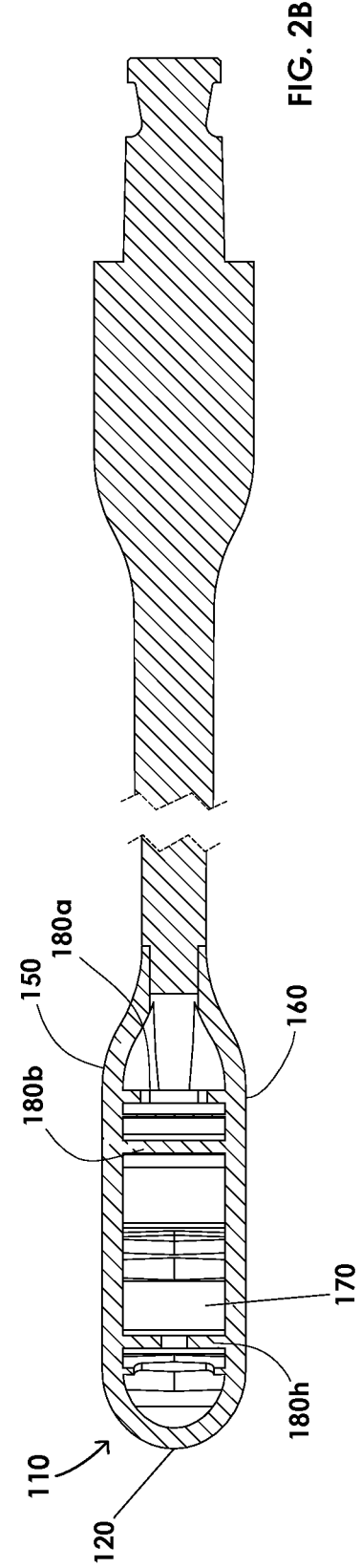

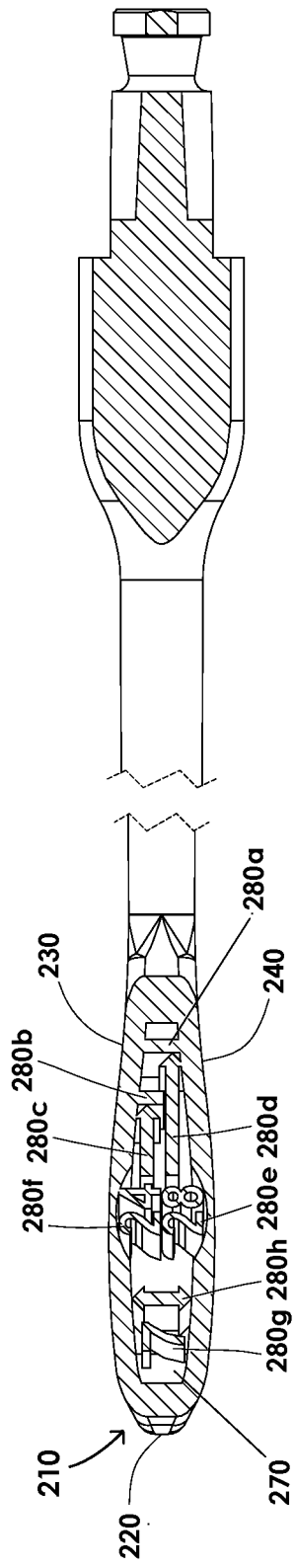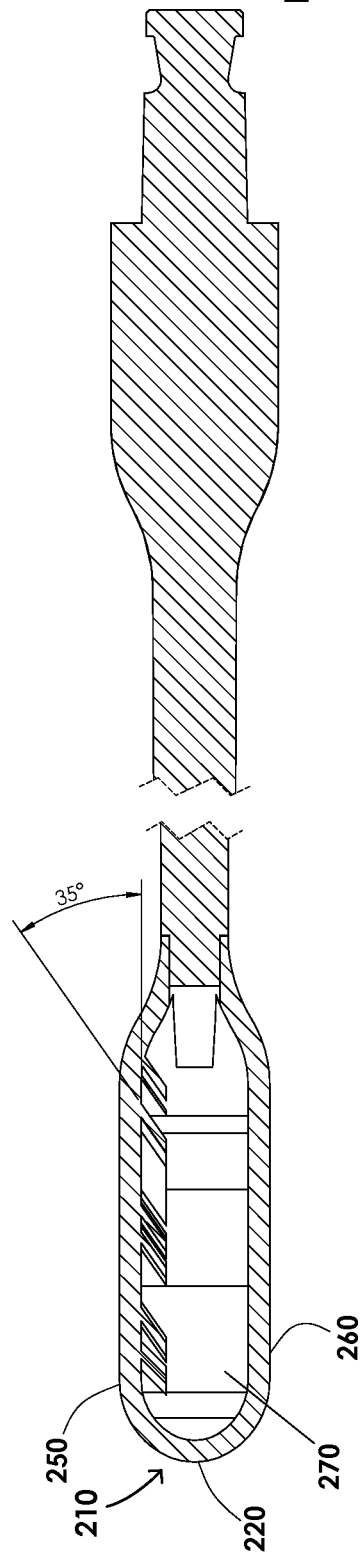

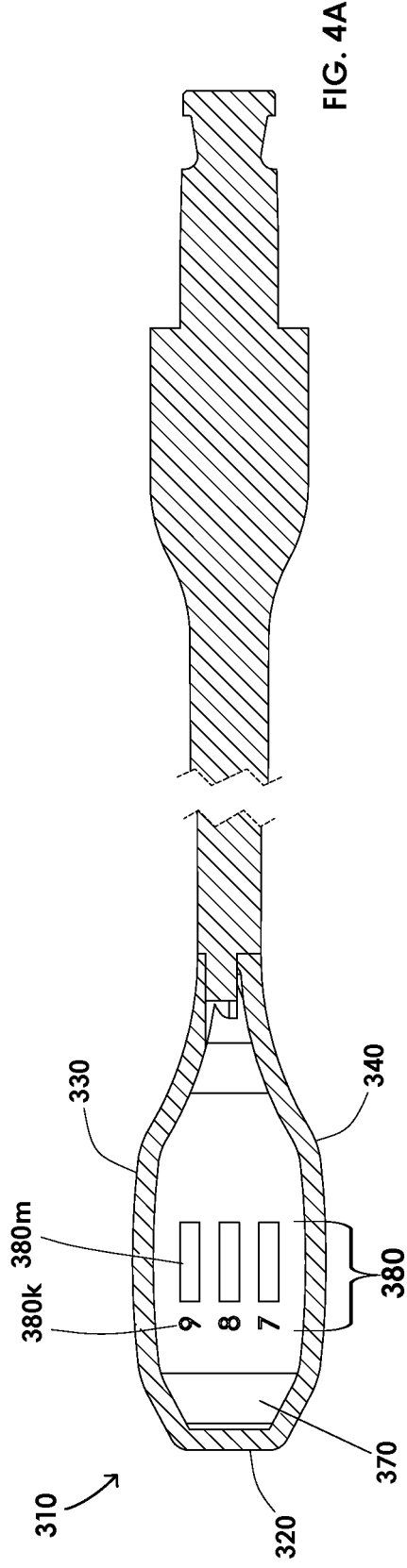

INTERVERTEBRAL TRIAL WITH MARKER

CROSS-REFERENCE TO RELATED APPLICATIONS

This application claims the benefit of the filing date of U.S. Provisional Patent Application No. 62/638,099 filed Mar. 3, 2018, the disclosure of which is hereby incorporated by reference herein in its entirety.

FIELD OF THE INVENTION

The present disclosure relates generally to an intervertebral trial including a front surface, a top surface, a bottom surface, and two side surfaces defining an internal space, where the internal space includes at least one marker.

BACKGROUND OF THE INVENTION

During surgery, it may be difficult for a surgeon to accurately select an appropriately sized prosthetic spinal implant. Due to the enclosed nature of the spinal column, it is virtually impossible for the surgeon to accurately evaluate the size and shape of a particular intervertebral disc space. In this regard, X-rays reveal little, if any, of the details of a discal region. As a result, the surgeon is normally forced to estimate the size of the disc space based upon the patient's height, weight and the particular intradiscal space in question. While this method of estimation is normally sufficient, occasionally an incorrectly sized prosthesis is selected, leading to possible problems. If, for example, too large a prosthesis is chosen, the surgeon will be unable to optimally position the device within the disc space. In fact, the surgeon may find it impossible to insert the prosthesis into the disc space or to achieve proper orientation. Conversely, where the selected prosthesis is too small, sufficient support may not be provided, potentially resulting in failure of the implantation. Unfortunately, in either case, the surgeon will not be aware of the sizing problem until after he or she has attempted to implant the prosthetic.

An intervertebral trial with external laser markings has been previously used to select a properly sized prosthetic. However, after insertion into the disc space, a surgeon is no longer able to visualize the external laser markings and therefore still cannot determine the appropriate size. Additionally, the laser markings can fade away after a few cleaning and autoclaving cycles making their visualization difficult.

Thus, there is a need for an improved intervertebral trial that may be used to identify the appropriate size of an intervertebral implant to be implanted into a patient.

BRIEF SUMMARY OF THE INVENTION

In an aspect, there is disclosed an intervertebral trial including a front surface, a top surface, a bottom surface, and two side surfaces defining an internal space, where the internal space includes at least one marker.

In one embodiment, an intervertebral trial includes a front surface, a top surface, a bottom surface, a first side surface and a second side surface defining an internal space. The internal space includes at least one marker structure attached to at least one of the top surface, the bottom surface, the first side surface and the second side surface. The at least one marker structure visually indicates a dimension of the intervertebral trial and the at least one marker structure is spatially representative of the dimension when measured relative to one of the front surface, the top surface, the bottom surface, the first side surface or the second side surface.

In some embodiments, the at least one marker structure may be radiopaque. In some embodiments, the at least one marker structure may be attached to posts that extend from the top surface to the bottom surface. In some embodiments, the at least one marker structure may include a marker structure shaped in the form of a number. In some embodiments, the at least one marker structure may include a marker structure shaped in the form of a symbol. In some embodiments, the at least one marker structure may include a first marker structure shaped in the form of a number and a second marker structure shaped in the form of a symbol. In some embodiments, the first marker structure and the second marker structure may both indicate the dimension. In some embodiments, the at least one marker structure may not be attached to one of the first side surface and the second side surface. In some embodiments, the at least one marker structure may extend between the first side surface and the second side surface. In some embodiments, the dimension may be a height of the intervertebral trial. In some embodiments, the at least one marker structure may extend into the internal space at an oblique angle from one of the first side surface and the second side surface. In some embodiments, the oblique angle may be about 35° from a longitudinal axis of the trial. In some embodiments, the dimension may represent one of height, length, and size of the trial. In some embodiments, the at least one marker structure may be attached to each of the top surface, the bottom surface, the first side surface and the second side surface.

In one embodiment, an intervertebral trial includes a body with a front surface, a top surface, a bottom surface, a first side surface and a second side surface defining an internal space. The at least one marker structure is disposed in the internal space and is attached to at least one of the top surface, the bottom surface, the first side surface and the second side surface. Further, the at least one marker structure is oriented orthogonally relative to one or both of the top surface and the bottom surface. The at least one marker structure is made of a material detectable through performance of an imaging process.

In some embodiments, the at least one marker structure may be shaped in the form of at least one of a number and a symbol. In some embodiments, the at least one marker structure may include a first marker structure shaped in the form of a number and a second marker structure shaped in the form of a line. The number may have a value representing a predetermined dimension that is defined by a distance between the line and one of the surfaces of the trial. In some embodiments, the at least one marker structure may include a third marker structure shaped in the form of a second number and a fourth marker structure shaped in the form of a second line. The second number may have a second value representing a second predetermined dimension different from the first predetermined dimension. The second predetermined dimension may be defined by a distance between the second line and one of the surfaces of the trial.

In some embodiments, the at least one marker structure may include a first marker structure indicating a first partial dimension of the trial and a second marker structure aligned with the first marker structure indicating a second partial dimension of the trial different from the first partial dimension. Each of the first partial dimension and the second partial dimension may be measured in the same direction.

It is to be understood that both the foregoing general description and the following detailed description are exemplary and explanatory only and are not restrictive of the embodiments of the disclosure, as claimed.

BRIEF DESCRIPTION OF THE DRAWINGS

Various embodiments of the present disclosure are described herein below with reference to the drawings, wherein:

FIG. 1A is a top view of an intervertebral trial according to one embodiment of the disclosure;

FIG. 1B is a cross-section of the intervertebral trial of FIG. 1A;

FIG. 1C is a side view of the intervertebral trial of FIG. 1A;

FIG. 1D is a cross-section of the intervertebral trial as shown in FIG. 1C;

FIG. 2A is a cross-section of an intervertebral trial according to one embodiment of the disclosure;

FIG. 2B is another cross-section of the intervertebral trial of FIG. 2A;

FIG. 3A is a cross-section of an intervertebral trial according to one embodiment of the disclosure;

FIG. 3B is another cross-section of the intervertebral trial of FIG. 3A;

FIG. 4A is a cross-section of an intervertebral trial according to one embodiment of the disclosure;

DETAILED DESCRIPTION

Figure 4B:
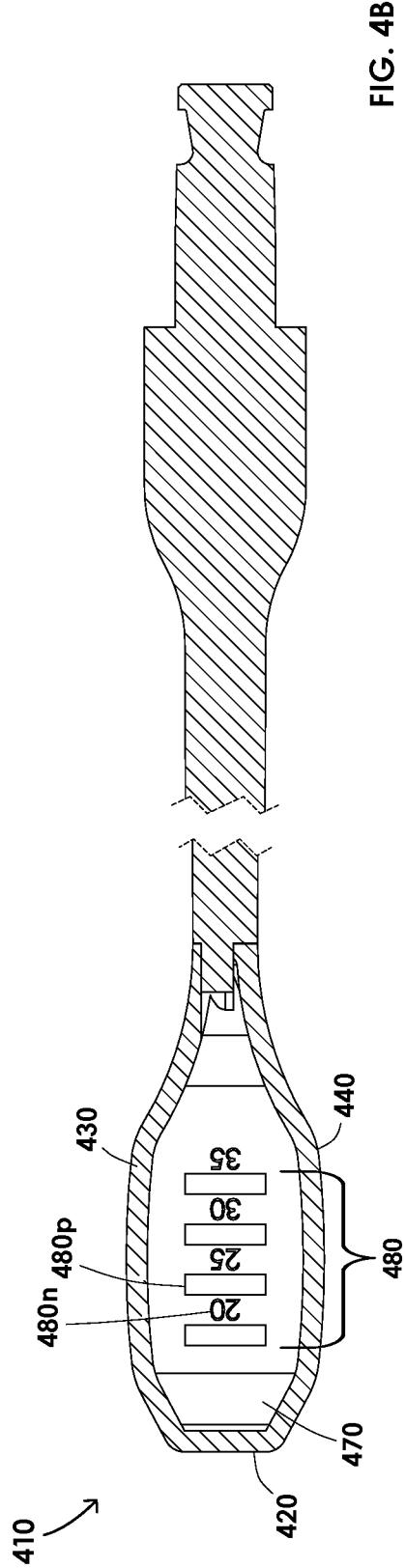
FIG. 4B is a cross-section of an intervertebral trial according to one embodiment of the disclosure.

Various embodiments will now be described in detail with reference to the drawings, wherein like reference numerals identify similar or identical elements. Additionally, in the drawings and in the description that follows, terms such as front, rear, upper, lower, top, bottom, and the similar directional terms are used simply for convenience of description and are not intended to limit the disclosure attached hereto. In the drawings and in the description that follows, the term "proximal" refers to the portion of the device that is closest to the operator, while the term "distal" refers to the portion of the device that is furthest from the operator. Additionally, in the drawings and in the description that follows, terms such as front, rear, upper, lower, top, bottom, and the similar directional terms are used simply for convenience of description and are not intended to limit the disclosure attached hereto. In addition, the term "cephalad" is used to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

In one aspect, the present disclosure relates to an intervertebral trial. Referring to FIGS. 1A-1D, there is disclosed one embodiment of an intervertebral trial 10 comprising a front surface 20, a top surface 30, a bottom surface 40, and two side surfaces 50, 60 defining an internal space 70. The internal space includes at least one marker. In FIG. 1B, two sets of markers 80 are shown. Throughout the disclosure, any part or whole of a marker may also be referred to as a marker structure. The intervertebral trial 10 can be inserted into an intervertebral space between adjacent, upper and lower vertebral bodies. The intervertebral trial 10 can have a generally rounded front surface, and a generally flat top and bottom surfaces 30 and 40, as shown in FIGS. 1A-3B. In another aspect, the intervertebral trial 10 can have a generally flat front surface, as shown in FIG. 4. The outer surfaces of the intervertebral trial present a generally smooth, continuous periphery for smooth insertion thereof into an intervertebral space.

The position of the intervertebral trial 10 can be determined using an imaging process, such as x-rays and/or fluoroscopy, to view the orientation of the intervertebral trial 10. At least one marker structure disposed in the internal space 70 allows a surgeon to identify the position of the intervertebral trial 10. The at least one marker structure can be made of a material that is detectable in the imaging process, such as a metal or a radiopaque material. Non-limiting examples of a radiopaque material include iodine, barium, tantalum, zirconium, titanium, bismuth, vanadium, chromium, iron, cobalt, nickel, copper, bromine, niobium, molybdenum, silver, tungsten, platinum, gold, and mixtures thereof. Metallic elements useful for biocompatibility and radiopacity include titanium, zirconium, tantalum, and platinum. Organic elements useful for biocompatibility and radiopacity include bromine, iodine, barium, and bismuth.

The at least one marker structure can include an oxide or salt material having at least one element with an atomic number of from about 22 to about 83. The at least one marker structure may include bismuth trioxide, diatrizoate sodium, barium sulfate, iodide, titanium oxide, zirconium oxide, stainless steel, or combinations thereof.

The at least one marker structure can include metals, polymers, copolymers, ceramics, or combinations thereof. Another type of marker structure includes a combination of titanium, tantalum, zirconium, platinum, or oxides thereof, for example in the form of a powder with or without a polymer matrix. Polyethylene or silicone are examples of biocompatible polymers that could be used as a matrix material.

The at least one marker structure can represent any dimension of the intervertebral trial 10, such as height, length, and size. Additionally, the at least one marker structure can include numbers, symbols, lines and combinations thereof. For instance, returning to the embodiment shown in FIGS. 1B and 1D, the two sets of markers 80 include numbers, symbols and lines. Structures of the two sets of markers 80 are attached to supporting posts 90 that extend from the top surface 30 to the bottom surface 40. The supporting posts 90 can be configured and dimensioned to be de minimus to avoid appearing in an image, but still provide the structural support to the marker structures. It should be appreciated that although certain embodiments of the disclosure do not depict or describe supporting posts, it is contemplated that such posts may be included with one or more of the marker structures of any given embodiment.

Viewing FIG. 1B from left to right are two sets of markers. A first set of markers includes a first marker structure 80*f* shaped in the form of a number "24", a second marker structure 80*c* shaped in the form of an arrow pointing to the right relative to the first marker structure, and a third marker structure 80*b* shaped to define a vertical line. In this and other illustrated embodiments, each of the number "2"

and "4" that constitute the first marker structure 80f are physically separate elements, although it is contemplated that the combined number may also be formed of a single element. For example, a marker structure may include an interconnecting part extending between the number "2" and the number "4." Each marker structure in this set of markers indicates a length of the trial 10. This length may be represented by the numerical value of the number. For example, the first marker structure shaped in the form of the number "24" may represent a length of 24 mm. In an aspect, the length of the trial, for example, for a posterior interbody, can be measured from the front surface 20 to a center of the vertical line of the third marker structure 80b. In another aspect, the length of the trial, for example, for a lateral cage, can be measured from a line after a blunt front end (not shown) to a center of the vertical line of the third marker structure 80b.

Similar to the first set of markers, a second set of markers includes a first marker structure 80e shaped in the form of a number "28", a second marker structure 80d shaped in the form of an arrow pointing to the right relative to the first marker structure, and a third marker structure 80a shaped to define a vertical line. Each of the number "2" and "8" that constitute the first marker structure 80e are physically separate elements, but may also be a combined single element. Each marker structure in this set of markers indicates the length of the trial 10 from the front surface 20 to a center of the vertical line of the third marker structure 80a. For example, the first marker structure 80e may indicate that the length of the trial is 28 mm. Visualization of a distance between the front end and the center of vertical line 80a may be used in situ to associate the length of the trial with relevant anatomy in a patient. As shown in FIGS. 1B and 1D, the structures 80a-f of the two sets of markers 80 do not attach to either of the two side surfaces.

In another embodiment shown in FIGS. 2A and 2B, an intervertebral trial 110 includes three sets of markers. In FIGS. 2A and 2B, like reference numerals refer to like elements, and unless otherwise indicated, referenced elements may be as described for trial 10, but within the 100-series of numbers. The first set of markers includes a first marker structure 180f shaped in the form of a number "24", a second marker structure 180c shaped in the form of an arrow pointing to the right relative to the first marker structure, and a third marker structure 180b shaped to define a vertical line. Each marker structure in this set of markers indicates the length of the trial 110 from the front surface 120 to a center of the vertical line of the third marker structure 180b. The second set of markers includes a first marker structure 180e shaped in the form of a number "28", a second marker structure 180d shaped in the form of an arrow pointing to the right relative to the first marker structure, and a third marker structure 180a shaped to define a vertical line. Each marker structure in this set of markers indicates the length of the trial 110 from the front surface 120 to a center of the vertical line of the third marker structure 180a. The third set of markers includes a first marker structure 180g shaped in the form of a number "7" and a second marker structure 180h in the form of a double-ended arrow that extends from the top surface 130 to the bottom surface 140. Each marker structure in this set of markers indicates the height of the trial 110 from the top surface 130 to the bottom surface 140. Each set of markers extends between the two side surfaces 150 and 160.

In another embodiment shown in FIGS. 3A-3B, a trial 210 includes marker structures 280a-h that extend at an oblique angle from one of the two sides surfaces. In FIGS. 3A and 3B, like reference numerals refer to like elements, and unless otherwise indicated, referenced elements may be as described for trial 10, but within the 200-series of numbers. In some examples, the oblique angle can range from about 10 to about 45°. In other examples, the angle can range from about 5° to about 40°. In still further examples, the angle can range from about 10° to about 35° relative to a longitudinal axis of the intervertebral trial 210.

In another embodiment shown in FIG. 4A, a trial 310 has a set of markers 380. In FIG. 4A, like reference numerals refer to like elements, and unless otherwise indicated, referenced elements may be as described for trial 10, but within the 300-series of numbers. The set of markers 380 includes a first marker structure 380k shaped in the form of a series of numbers and a second marker structure 380m shaped in the form of a series of horizontal lines. The numbers of first marker structure 380k and corresponding horizontal lines of second marker structure 380m can function as a ruler indicating a distance from a respective horizontal line and one of a top surface 330 or a bottom surface 340 of the trial 310. For example, as shown in FIG. 4A, the horizontal line of the second marker structure 380m aligned with the number "9" of the first marker structure 380k can represent a distance of 9 mm from a center of the horizontal line to the bottom surface 340.

In yet another embodiment, as shown in FIG. 4B, a trial has a set of markers 480. In FIG. 4B, like reference numerals refer to like elements, and unless otherwise indicated, referenced elements may be as described for trial 10, but within the 400-series of numbers. The set of markers 480 includes a first marker structure 480n shaped in the form of a series of numbers and a second marker structure 480p shaped in the form of a series of vertical lines. The numbers of the first marker structure 480n and corresponding vertical lines of the second marker structure 480p can function as a ruler indicating a distance from a front surface 420 to the corresponding vertical line preceding the number 480n on a side of the number closer to the front end 420. Alternatively, a location of the number relative to the vertical line may be reversed.

Figure 5A:
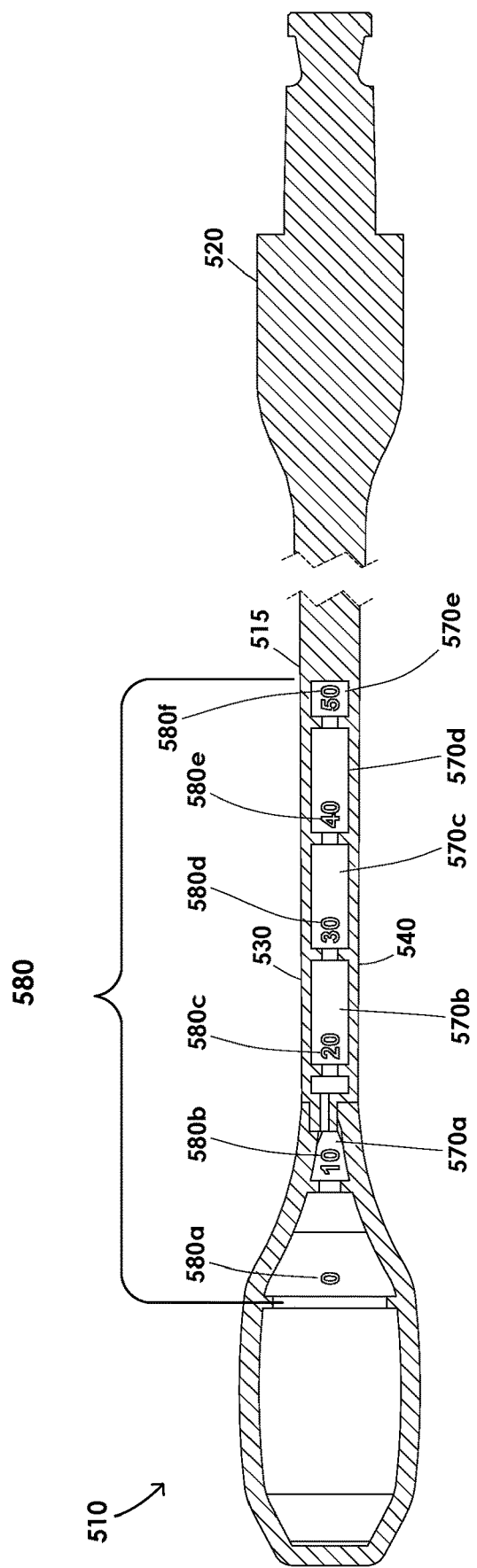
FIG. 5A is a cross-section of an intervertebral trial according to one embodiment of the disclosure.
Figure 5B:
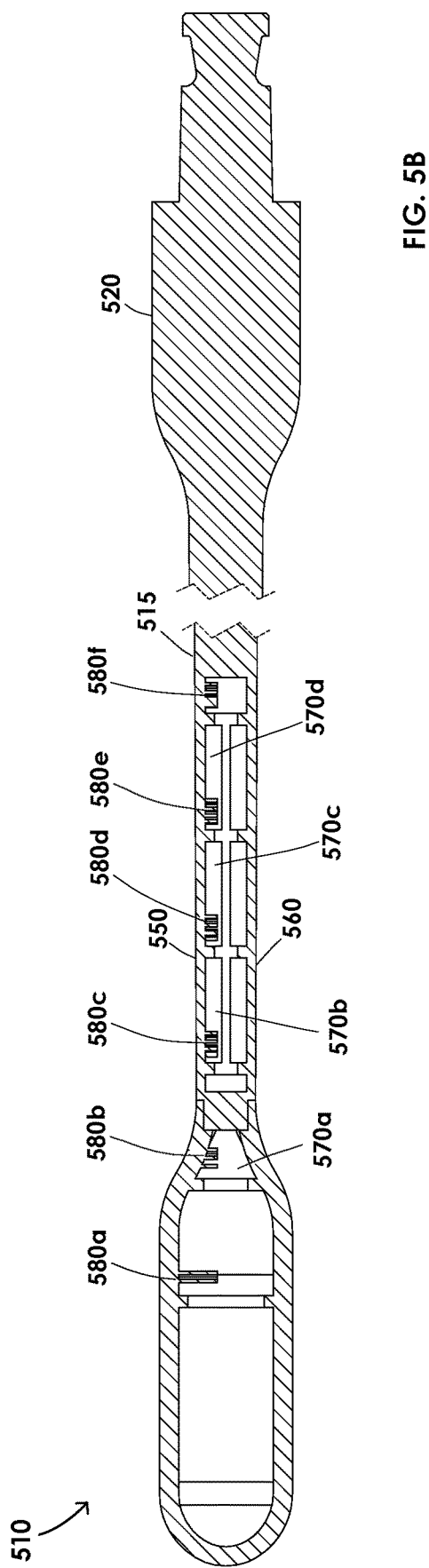
FIG. 5B is another cross-section of the intervertebral trial of FIG. 5A.

In another embodiment, FIGS. 5A and 5B illustrate an intervertebral trial 510. In FIGS. 5A and 5B, like reference numerals refer to like elements, and unless otherwise indicated, referenced elements may be as described for trial 10, but within the 500-series of numbers. Trial 510 includes a shaft 515 that extends into a handle 520. The shaft 515 also includes a top surface 530, a bottom surface 540, and two side surfaces 550, 560 defining internal spaces 570. Collectively, the internal spaces 570 include a set of markers 580. Alternatively, the trial may have a single internal space. The set of markers 580 includes a plurality of marker structures 580a-f that are shaped in the form of numbers, each number indicating a depth of an intervertebral space within the patient or a depth of a predetermined location on the trial when the trial is only advanced partially toward the intervertebral space. In this arrangement, a marker structure is present in a single internal space. For example, as shown in FIG. 5A, marker structure 580b shaped in the form of a number "10" is present in internal space 570a, and marker structure 580c shaped in the form of a number "20" is present in internal space 570b. As shown in FIG. 5A, a similar positioning also exists for marker structures 580d-f. The marker structures 580a-f extend from a single side surface 550, as shown in FIG. 5B.

In another embodiment, an intervertebral trial includes at least one marker structure in the form of a number or a symbol that is disposed in an internal space and is oriented so that it is visible looking toward a front end of the intervertebral trial. Put another way, in one example, where the marker structure is shaped in the form of a number, a width of the number extends between side surfaces of the trial. In this manner, the number is oriented at a ninety degree angle relative to the marker structures of FIGS. 1A-1D, for example.

The intervertebral trial may be varied in many ways. For example, an intervertebral trial may include one or more marker structures. Further, any number of marker structures or sets of markers in an intervertebral trial may: Extend from a single side of an internal space within the trial; extend between two opposing sides of an internal space within the trial; or extend from four sides of an internal space within the trial. In this manner, an intervertebral trial with more than one marker structure may have one marker structure that extends from a single side of the internal space and another marker structure that extends from two opposing sides, and so on. To the extent that the internal space is defined by more than four surfaces, the above contemplated arrangements may be further varied accordingly. Thus, for example, an internal space with six sides may have a marker structure that extends from five of the six sides. Further, for purposes of clarity, to the extent that a marker structure may extend from any number of surfaces within a trial, the marker structure may also be attached to any number of surfaces.

One advantage of the intervertebral trial includes the ability to identify dimensions relative to the anatomy while the trial is positioned in an intervertebral space. Another advantage derives from the internal positioning of the marker within the trial. Through this arrangement, the marker of the trial is less prone to deterioration through wear and tear than markers on a surface of a trial, for example.

In another aspect, a trial includes at least one marker structure along with its mirror image. In this manner, the at least one marker structure can be seen in an image from either side of the trial.

In yet another aspect, a method of trialing an intervertebral disc space is performed with the intervertebral trial described in the present disclosure. In one embodiment utilizing trial 10, the method includes a) creating the disc space, b) inserting an intervertebral trial 10 into the disc space, and c) imaging the intervertebral disc space to view at least one marker structure of the two sets of markers 80 present within the internal space 70 of the intervertebral trial 10. In this manner, a dimension within the intervertebral disc space may be verified. This method may also be performed in a similar manner using any other trial contemplated in the present disclosure, including intervertebral trials 110, 210, 310, 410, 510.

The intervertebral trials contemplated in the present disclosure, including trials 10, 110, 210, 310, 410, 510, can be formed of any material that is bio-compatible and can include a radiopaque material to form at least one marker structure within the trial. The intervertebral trial 10, 110, 210, 310, 410, 510 can be formed by known manufacturing methods, such as additive manufacturing, e.g., three-dimensional printing; chemical etching; photo etching; laser cutting; water jet cutting; and traditional machining, etc.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An intervertebral trial comprising a front surface, a top surface,
a bottom surface, a first side surface and a second side surface defining an internal space,
wherein the internal space includes at least one marker structure attached to at least one of the top surface, the bottom surface, the first side surface and the second side surface, the at least one marker structure having first and second locations thereon, the first location being a first minimum distance from the surface to which the at least one marker structure is attached and the second location being a second minimum distance from the surface to which the at least one marker structure is attached, the second minimum distance being different from the first minimum distance,
wherein the at least one marker structure visually indicates a dimension of the intervertebral trial, and
wherein the at least one marker structure is spatially representative of the dimension when measured relative to one of the front surface, the top surface, the bottom surface, the first side surface or the second side surface.

2. The intervertebral trial of claim 1, wherein the at least one marker structure is radiopaque.

3. The intervertebral trial of claim 1, wherein the at least one marker structure is attached to posts that extend from the top surface to the bottom surface.

4. The intervertebral trial of claim 1, wherein the at least one marker structure includes a marker structure shaped in the form of one of a number and a symbol.

5. The intervertebral trial of claim 1, wherein the at least one marker structure includes a first marker structure shaped in the form of a number and a second marker structure shaped in the form of a symbol.

6. The intervertebral trial of claim 5, wherein the first marker structure and the second marker structure both indicate the dimension.

7. The intervertebral trial of claim 1, wherein the at least one marker structure is not attached to one of the first side surface and the second side surface.

8. The intervertebral trial of claim 1, wherein the at least one marker structure extends between the first side surface and the second side surface.

9. The intervertebral trial of claim 1, wherein the dimension is a height of the intervertebral trial.

10. The intervertebral trial of claim 1, wherein the at least one marker structure extends into the internal space at an oblique angle from one of the first side surface and the second side surface.

11. The intervertebral trial of claim 10, wherein the oblique angle is about 35° from a longitudinal axis of the trial.

12. The intervertebral trial of claim 1, wherein the dimension represents one of height, length, and size.

13. The intervertebral trial of claim 1, wherein the at least one marker structure is attached to each of the top surface, the bottom surface, the first side surface and the second side surface.

14. The intervertebral trial of claim 1, wherein the internal space is a fully enclosed cavity.

15. An intervertebral trial comprising:
a body including a front surface, a top surface, a bottom surface, a first side surface and a second side surface defining an internal space; and
at least one marker structure disposed in the internal space, the at least one marker structure attached to at least one of the top surface and the bottom surface, and the at least one marker structure oriented orthogonally relative to the at least one of the top surface and the bottom surface to which the at least one marker is attached,
wherein the at least one marker structure is made of a material detectable through performance of an imaging process.

16. The intervertebral trial of claim 15, wherein the at least one marker structure is shaped in the form of at least one of a number and a symbol.

17. The intervertebral trial of claim 15, wherein the at least one marker structure includes a first marker structure shaped in the form of a number and a second marker structure shaped in the form of a line, the number having a value representing a predetermined dimension that is defined by a distance between the line and one of the surfaces of the trial.

18. The intervertebral trial of claim 17, wherein the at least one marker structure includes a third marker structure shaped in the form of a second number and a fourth marker structure shaped in the form of a second line, the second number having a second value representing a second predetermined dimension different from the first predetermined dimension, the second predetermined dimension defined by a distance between the second line and one of the surfaces of the trial.

19. The intervertebral trial of claim 15, wherein the at least one marker structure includes a first marker structure indicating a first partial dimension of the trial and a second marker structure aligned with the first marker structure indicating a second partial dimension of the trial different from the first partial dimension, each of the first partial dimension and the second partial dimension being measured in the same direction.

20. An intervertebral trial comprising:
a body with a front surface, a top surface, a bottom surface, a first side surface and a second side surface defining an internal space,
at least one marker structure disposed in the internal space, the at least one marker structure attached to a post that extends from one of the front surface, the top surface, the bottom surface, the first side surface and the second side surface,
wherein the at least one marker structure visually indicates a dimension of the intervertebral trial, and
wherein the at least one marker structure is spatially representative of the dimension when measured relative to one of the front surface, the top surface, the bottom surface, the first side surface or the second side surface.

* * * * *